US008423387B1

(12) United States Patent
Mirza

(10) Patent No.: US 8,423,387 B1
(45) Date of Patent: Apr. 16, 2013

(54) DIRECT PHYSICIAN DELIVERY OF PATIENT CARE OVER A NETWORK

(76) Inventor: Muhammad Mirza, Cedar Grove, NJ (US)

( * ) Notice: Subject to any disclaimer, the term of this patent is extended or adjusted under 35 U.S.C. 154(b) by 0 days.

(21) Appl. No.: 13/476,504

(22) Filed: May 21, 2012

Related U.S. Application Data

(60) Provisional application No. 61/506,419, filed on Jul. 11, 2011.

(51) Int. Cl.
    *G06F 19/00* (2011.01)
(52) U.S. Cl.
    USPC .............................................. 705/3
(58) Field of Classification Search .............. 705/2, 3; 707/104.1; 600/300
    See application file for complete search history.

(56) References Cited

U.S. PATENT DOCUMENTS

| | | | |
|---|---|---|---|
| 6,014,629 A * | 1/2000 | DeBruin-Ashton | 705/2 |
| 7,389,245 B1 * | 6/2008 | Ashford et al. | 705/2 |
| 2002/0188179 A1 * | 12/2002 | Bulat | 600/300 |
| 2005/0182653 A1 | 8/2005 | Urban et al. | |
| 2006/0184524 A1 | 8/2006 | Pollanz | |
| 2006/0271400 A1 * | 11/2006 | Clements et al. | 705/2 |
| 2007/0038477 A1 * | 2/2007 | Kelly et al. | 705/3 |
| 2008/0004499 A1 * | 1/2008 | Davis | 600/300 |
| 2008/0147741 A1 * | 6/2008 | Gonen et al. | 707/104.1 |
| 2009/0125326 A1 * | 5/2009 | Wasson et al. | 705/2 |
| 2009/0132813 A1 | 5/2009 | Schibuk | |
| 2009/0171227 A1 | 7/2009 | Dziubinski et al. | |
| 2009/0240527 A1 * | 9/2009 | Bluth | 705/3 |
| 2009/0271378 A1 | 10/2009 | Witherspoon | |
| 2010/0205005 A1 | 8/2010 | Pritchett et al. | |
| 2010/0250271 A1 | 9/2010 | Pearce et al. | |
| 2010/0287001 A1 | 11/2010 | Pearce et al. | |

OTHER PUBLICATIONS

Dizik, Alina; "A Doctor's Visit Without the Cold Stethoscope" Wall Street Journal, Aug. 7, 2012, p. D5, Dow Jones & Company, Inc., USA.

\* cited by examiner

*Primary Examiner* — John Pauls
(74) *Attorney, Agent, or Firm* — Goldstein Law Offices, P.C.

(57) ABSTRACT

A system and method of providing delivery of medical care through instant patient access to a physician via an application (app) on a smartphone connecting over a network. A patient signs into the system through a smartphone app and selects a category for an emerging medical issue and further submits a detailed description of the presenting issue. A physician instantly receives a notice through the app on a physician smartphone that the patient is waiting a consultation. The physician opens the app, reviews the category and the detailed description and calls the patient directly through the app for a consultation. After the consultation is complete, the physician submits clinical advice through the app, the app electronically mailing the patient with the advice in writing. The physician also submits a prescription to a pharmacy, makes a referral, bills an insurance provider and accepts payment through the app.

20 Claims, 10 Drawing Sheets

DIRECT PHYSICIAN DELIVERY OF PATIENT CARE OVER A NETWORK

CROSS-REFERENCE TO RELATED APPLICATIONS

This application claims the benefit of U.S. Provisional Application Ser. No. 61/506,419, filed on Jul. 11, 2011, which is herein incorporated by reference in its entirety for all purposes.

TECHNICAL FIELD

Generally, the present disclosure relates to a system and method of providing direct physician delivery of patient care. More particularly, the present disclosure relates to a system and method of providing delivery of medical care through instant patient access to a physician through an application on a smartphone connecting over a network.

BACKGROUND

Healthcare costs continue to rise, forcing insurers, including government-provided programs, such as Medicare and Medicaid, to limit coverage, raise premiums or increase co-payments. Healthcare costs are greater than 15% of our Gross Domestic Product (GDP) and are a major factor in the health of the economy as well as the health of the nation. Nearly half of those costs are covered by government programs, such as Medicare and Medicaid. In addition to the soaring cost, rising unemployment, with many losing health insurance while unemployed, as well as the rise of obesity of almost epidemic proportions has severely hampered the healthcare delivery system. There is clearly a demand for efficiently delivered healthcare that provides quality care needed to maintain the health of all segments of society.

Over one-third of healthcare costs come from administrative services. Within the conventional physician's office, there are non-medical staff members, such as receptionist, insurance specialists, administrative assistants, answering service and appointment clerks who are not directly involved with patient care. The staff often creates a gap between the patient and the physician, blocking channels of communication and delaying timely access to the healthcare system.

An additional source of costs in the healthcare system is the frequent use of emergency room (ER) in place of a primary care physician. Many ER patients present routine medical needs because they lack timely access to a healthcare provider, substituting the ER for an ongoing relationship with a physician. These routine needs tie up the ER, a facility designed for urgent and life-threatening situations, staffed by high-priced specialists and equipped with expensive high-tech instruments, create unimaginable waste in the system.

The medical establishment has slowly adopted technology for managing patient medical histories that are accessible over a network. For example, Pollanz (U.S. Patent Application Publication 2006/0184524) discloses a secure and independent medical database system. Pritchett et al. (U.S. Patent Application Publication 2010/0205005) discloses a medical record management system on the Internet that also stores family medical history for access by physicians. Witherspoon (U.S. Patent Application Publication 2009/0271378) developed a system for identifying and contacting medical personnel and communicating via video relevant information for emergency treatment of a patient. Similarly, Dziubinski et al. (U.S. Patent Application Publication 2009/0171227) has disclosed a system of processing an ECG (electrocardiogram) signal and transmitting the signal over a network.

There have been other systems relating to patient treatment, such as patient reminder to follow a medicine dosage regimen, disclosed in Urban et al. (U.S. Patent Application Publication 2005/0182653). Pearce et al. (U.S. Patent Application Publications 2010/0250271, 2010/0287001) uses a network application for capturing and transmitting data, including real-time pulse rate and temperature data. All these systems rely on a method of securing transmitting data and making transactions over a secure network as disclosed in Shibuk (U.S. Patent Application Publication 2009/0132813.)

All of the above disclosures focus on capturing, storing and presenting data, but none facilitate communication between the physician and the patient. None eliminate non-medical personnel from impinging on the patient-physician relationship by being gatekeepers and intruders. None reduce the cost or increase the efficiency of healthcare delivery and in many cases, have the opposite effect on healthcare delivery and quality.

Accordingly, there is a need to address at least one of the above or other disadvantages.

BRIEF SUMMARY

It is an aspect of an example embodiment of the present disclosure to produce a system that lowers costs of healthcare delivery. Accordingly, the present disclosure discloses a method and a system for direct physician patient care delivery that reduces administrative costs in healthcare delivery by eliminating non-physician staff in the administration of healthcare delivery.

It is another aspect of an example embodiment of the present disclosure to produce a system that provides to a patient instant access to a physician. Accordingly, the present disclosure discloses a method and a system for direct physician patient care delivery that provides access to a physician through an app on the smartphone of the physician, contacting the physician directly.

It is a further aspect of an example embodiment of the present disclosure to produce a system that provides a homebound patient access to a physician. Accordingly, the present disclosure discloses a method and a system for direct physician patient care delivery that that provides access to a physician through an app on the smartphone of the physician, so that a home-bound patient contacts the physician directly over a network without leaving the patient's home.

It is yet another aspect of an example embodiment of the present disclosure to produce a system that lowers costs of healthcare delivery. Accordingly, the present disclosure discloses a method and a system for direct physician patient care delivery that decreases patient hospitalization and emergency room utilization by providing a patient instant access to a physician, preventing complications and providing accessible healthcare, thus lowering costs.

It is yet a further aspect of an example embodiment of the present disclosure to produce a system that refers a patient to a specialist instantly and directly. Accordingly, the present disclosure discloses a method and a system for direct physician patient care delivery that by providing a physician instant access to a specialist physician for consultation, preventing complications and providing accessible healthcare, thus lowering costs.

It is still another aspect of an example embodiment of the present disclosure to produce a system that creates a direct relationship between a doctor and a patient. Accordingly, the present disclosure discloses a method and a system for direct physician patient care delivery that provides a patient direct access to a physician without an administrative intermediary, closing a gap created by the intermediary in the relationship, thus establishing a direct relationship.

It is still a further aspect of an example embodiment of the present disclosure to produce a system that improves a relationship between a doctor and a patient. Accordingly, the present disclosure discloses a method and a system for direct physician patient care delivery that provides a patient direct access to a physician, improving communications between patient and physician, thus enhancing the quality of care provided, increasing patient compliance, decreasing a chance of a medical error through miscommunication, building a long-term relationship between patient and physician, thus increasing satisfaction for both patient and physician.

Example embodiments of the present disclosure include a system and a method of providing delivery of medical care through instant patient access to a physician via a software application (app) on a smartphone connecting over a network. A patient signs into the system through a smartphone app and selects a category for an emerging medical issue and further submits a detailed description of the presenting issue. A physician instantly receives a notice through the app on a physician smartphone that the patient is waiting a consultation. The physician opens the app, reviews the category and the detailed description and calls the patient directly through the app for a consultation. After the consultation is complete, the physician submits clinical advice through the app, the app electronically mailing the patient with the advice in writing. The physician also submits a prescription to a pharmacy, makes a referral, bills an insurance provider and accepts payment through the app.

An example embodiment of the present disclosure is a method of delivering medical care. The method includes maintaining, in a computer system, patient profiles associated with patients and physician profiles associated with physicians. Each of the patient profiles including medical history, voice communication information and text communication information. Each of the physician profiles including payee information. The method also includes receiving, from a first computing device, medical symptoms and payer information associated with one of the patient profiles. The system storing the symptoms in the history of the one of the patient profiles. The method further includes causing the symptoms to be displayed on a second computing device. The second device displaying a text field associated with one of the physician profiles. The system authorizing the one of the physician profiles to view the history of the one of the patient profiles. The method even further includes causing a voice datalink to be established, from the second device, according to the voice information of the one of the patient profiles in order to provide oral consultation regarding the symptoms. The method additionally includes causing a clinical advice, as entered into the field, to be sent according to the text information of the one of the patient profiles. The system storing the advice in the history of the one of the patient profiles. The advice memorializing the consultation. The system billing according to the payer information and the payee information of the one of the physicians.

Another example of the present disclosure is a system of delivering medical care. The system includes a computer system storing patient profiles corresponding to patients and physician profiles corresponding to physicians. Each of the patient profiles including medical history, voice communication information and text communication information. Each of the physician profiles including payee information. The system also includes a first mobile computing device running a first instance of a software application having a patient mode and a physician mode. The patient mode initiated via a patient login corresponding to one of the patient profiles. The physician mode initiated via a physician login corresponding to one of the physician profiles. The first instance running in the patient mode. The first instance sending medical symptoms and payer information to the computer system. The computer system storing the symptoms in the history of the one of the patient profiles. The system further includes a second mobile computing device running a second instance of the application in the physician mode. The second instance displaying the symptoms and a text field. The computer system authorizing the one of the physician profiles to view the history of the one of the patient profiles. The second instance establishing a voice datalink according to the voice information of the one of the patient profiles in order to provide oral consultation regarding the symptoms. The second instance sending a clinical advice, as input into the field, according to the text information of the one of the patient profiles. The advice memorializing the consultation. The computer system storing the advice in the history of the one of the patient profiles. The computer system billing according to the payer information and the payee information of the one of the physicians Yet another example embodiment of the present disclosure is a method of delivering medical care includes inputting a medical symptom and payer information associated with a patient profile into a first computing device. The patient profile including medical history, voice communication information and text communication information. The method also includes sending the symptoms and the payer information to a computer system for storing the symptoms in the history and the payee information in the patient profile. The method further includes retrieving, via a second computing device, the symptom from the system and displaying the symptom and a text field on the second device, the field associated with a physician profile storing payee information. The method even further includes authorizing, via the system, the physician profile to view the history. The method yet even further includes establishing a voice datalink, from the second device, according to the voice information in order to provide oral consultation regarding the symptoms. The method additionally includes sending a clinical advice, as entered into the field, according to the text information. The advice memorializing the consultation. The method even additionally includes storing, via the system, the advice in the history. The method further additionally includes billing, via the system, according to the payer information and the payee information.

To the accomplishment of the above and related aspects of the present disclosure may be embodied in the form illustrated in the accompanying drawings. Attention is called to the fact, however, that the drawings are illustrative only. Variations are contemplated as being part of the present disclosure.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
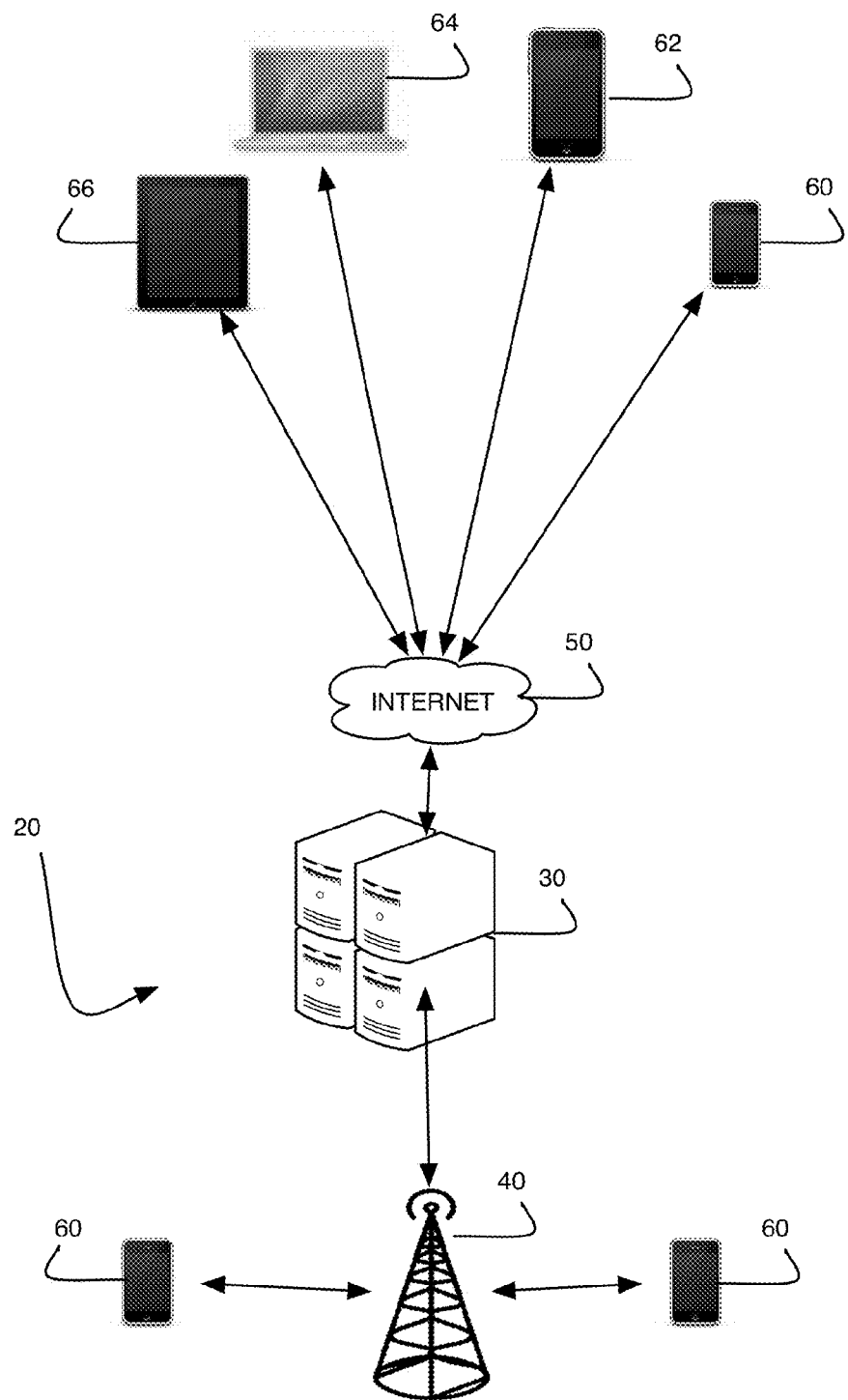
FIG. 1 shows a schematic diagram of an example embodiment of a direct physician patient care delivery system according to the present disclosure.

The present disclosure now will be described more fully hereinafter with reference to the accompanying drawings, in which various example embodiments are shown. This disclosure may, however, be embodied in many different forms, and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

An example embodiment of the present disclosure is a method of delivering medical care. The method includes maintaining, in a computer system, patient profiles associated with patients and physician profiles associated with physicians. Each of the patient profiles includes patient medical history, patient voice communication information and patient text communication information. Each of the physician profiles includes payee information. The method also includes receiving, from a first computing device, medical symptoms and payer information associated with one of the patient profiles. The system stores the symptoms in the history of the one of the patient profiles. The method further includes causing the symptoms to be displayed on a second computing device. The second device displaying a text field associated with one of the physician profiles. The system authorizes the one of the physician profiles to view the history of the one of the patient profiles. The method additionally includes causing a voice datalink to be established, from the second device, according to the voice information of the one of the patient profiles in order to provide oral consultation regarding the symptoms. The method even further includes causing clinical advice, as entered into the field, to be sent according to the text information of the one of the patient profiles. The system stores the advice in the history of the one of the patient profiles. The advice memorializes the consultation. The system bills according to the payer information and the payee information of the one of the physicians.

The method can include causing a patient waiting list associated with the one of the physician profiles to be displayed on the second device. The list listing indicia associated with the one of the patient profiles and another of the patient profiles. The system updating the list. The method can include receiving acknowledgement of activation of one of the indicia corresponding to the one of the patient profiles and performing the causing the symptoms to be displayed on the second device. The method can include causing an appointment to visit a physician associated with the one of the physician profiles to be scheduled on the second device. The symptoms including at least one of a symptom detailed description and a symptom image.

The method can include receiving physician credentials for the one of the physician profiles. The method can include verifying the credentials. The method can include causing prescription data to be sent from the second device to a third party provider. The prescription data relating to treatment of the symptoms. The system storing the prescription data in the history of the one of the patient profiles. The voice datalink including at least one of a phone call, a voice chat and a video teleconference.

The method can include causing a medical diagnostic test order for a patient associated with the one of the patient profiles to be placed on the second device. The method can include receiving a result of the test. The system storing the result in the history of the one of the patient profiles. The text information allowing at least one of printing out and mailing the advice, emailing the advice and texting the advice.

The method can include authorizing another physician profile to view the history of the one of the patient profiles. The physician profiles including the another physician profile. The patient profiles including medical insurance information. The payer information functions as co-payment according to the insurance information of the one of the patient profiles.

The method can include causing a referral to be sent from the second device to a specialist physician profile associated with a specialist physician. The physician profiles including the specialist physician profile. The system authorizing the specialist physician profile to view the history of the one of the patient profiles. The system storing the referral in the history of the one of the patient profiles. The symptoms including at least one of a medical category related to the symptoms and a common symptom associated with the category.

The method can include receiving data indicating a geographic location of the first device. The method can include causing a map to be displayed on the first device. The map showing which of the physicians are near the location. The physician profiles including physician pictures and recommendations as recommended via the patient profiles. The method can include selecting the one of the physicians as a default physician. The system causing the history of the one of the patients to be displayed on the second device in chronological order.

The method can include authorizing the one of the physician profiles to view the history of other patient profiles associated with other patients biologically related to the patient. The physician profiles including physician specialities.

The method can include removing the another of the patient profiles from the list in response to a removal action on the second device. The method can include causing a stage indicator to be displayed on at least one of the first device and the second device. The indicator visually indicating a stage of process in the delivery of medical care. The patient profiles including graphical representations of at least portion of the histories.

Another example embodiment of a system of delivering medical care. The system includes a computer system storing patient profiles corresponding to patients and physician profiles corresponding to physicians. Each of the patient profiles including medical history, voice communication information and text communication information. Each of the physician profiles including payee information. The system also includes a first mobile computing device running a first instance of a software application having a patient mode and a physician mode. The patient mode initiated via a patient login corresponding to one of the patient profiles. The physician mode initiated via a physician login corresponding to one of the physician profiles. The first instance running in the patient mode. The first instance sending medical symptoms and payer information to the computer system. The computer system storing the symptoms in the history of the one of the patient profiles. The system further includes a second mobile computing device running a second instance of the application in the physician mode. The second instance displaying the symptoms and a text field. The computer system authorizing the one of the physician profiles to view the history of the one of the patient profiles. The second instance establishing a voice datalink according to the voice information of the one of the patient profiles in order to provide oral consultation regarding the symptoms. The second instance sending a clinical advice, as input into the field, according to the text information of the one of the patient profiles. The advice memorializing the consultation. The computer system storing the advice in the history of the one of the patient profiles. The computer system billing according to the payer information and the payee information of the one of the physicians.

The system can include the second instance displaying a patient waiting list associated with the one of the physician profiles. The list listing indicia corresponding to the one of the patient profiles and another of the patient profiles. The computer system updating the list. The computer system receiving acknowledgement of activation of one of the indicia corresponding to the one of the patient profiles and, in response, the second instance displaying the symptoms. The second instance scheduling an appointment to visit a physician associated with the one of the physician profiles. The symptoms including at least one of a symptom detailed description and a symptom image.

The system can include the second instance sending prescription data to a third party provider. The prescription data relating to treatment of the symptoms. The computer system storing the prescription data in the history of the one of the patient profiles. The voice datalink including at least one of a phone call, a voice chat and a video teleconference.

The system can include the second instance placing a medical diagnostic test order for a patient associated with the one of the patient profiles. The computer system receiving a result of the test and storing the result in the history of the one of the patient profiles. The text information allowing for at least one of printing out and mailing the advice, emailing the advice and texting the advice.

The system can include the computer system authorizing another physician profile to view the history of the one of the patient profiles. The physician profiles including the another physician profile. Each of the patient profiles including medical insurance information. The payer information functioning as co-payment according to the insurance information of the one of the patient profiles.

The system can include the second instance sending a referral to a specialist physician profile associated with a specialist physician. The physician profiles including the specialist physician profile. The computer system authorizing the specialist physician profile to view the history of the one of the patient profiles. The computer system storing the referral in the history of the one of the patient profiles. The symptoms including at least one of a medical category related to the symptoms and a common symptom associated with the category.

The system can include the computer system receiving data indicating a geographic location of the first device. The first instance displaying a map showing which of the physicians are near the location. The physician profiles including physician pictures and recommendations as recommended via some of the patient profiles. The first instance selecting the one of the physicians as a default physician. The computer system causing the history of the one of the patients to be displayed via the second instance in chronological order.

The system can include the computer system authorizing for the one of the physician profiles to view the history of other patient profiles associated with other patients biologically related to the patient. The physician profiles including physician specialities.

The system can include at least one of the first instance and the second instance displaying a stage indicator visually indicating a stage in the delivery of medical care. The patient profiles including graphical representations of at least portion of the histories.

Yet another example embodiment of a method of delivering medical care includes inputting a medical symptom and payer information associated with a patient profile into a first computing device. The patient profile including medical history, voice communication information and text communication information. The method also includes sending the symptoms and the payer information to a computer system for storing the symptoms in the history and the payee information in the patient profile. The method further includes retrieving, via a second computing device, the symptom from the system and displaying the symptom and a text field on the second device, the field associated with a physician profile storing payee information. The method even further includes authorizing, via the system, the physician profile to view the history. The method yet even further includes establishing a voice datalink, from the second device, according to the voice information in order to provide oral consultation regarding the symptoms. The method additionally includes sending a clinical advice, as entered into the field, according to the text information. The advice memorializing the consultation. The method even additionally includes storing, via the system, the advice in the history. The method further additionally includes billing, via the system, according to the payer information and the payee information.

The method can include displaying a patient waiting list of the physician profile on the second device. The list listing indicia associated with the patient profile and another patient profile. In response to activating one of the indicia corresponding to the patient profile, displaying the symptom on the second device. Scheduling, via the second device, an appointment to visit a physician associated with the physician profile. Sending prescription data from the second device to a third party provider. The prescription data relating to treatment of the symptoms. The system storing the prescription data in the history. Placing, via the second device, a medical diagnostic test order for the patient profile. Authorizing, via the system, another physician profile to view the history, the patient profile including medical insurance information. The payer information functioning as co-payment according to the insurance information of the one of the patient profiles. Displaying, on at least one of the first device and the second device, a stage indicator visually indicating a stage in the delivery of medical care.

Figure 4:
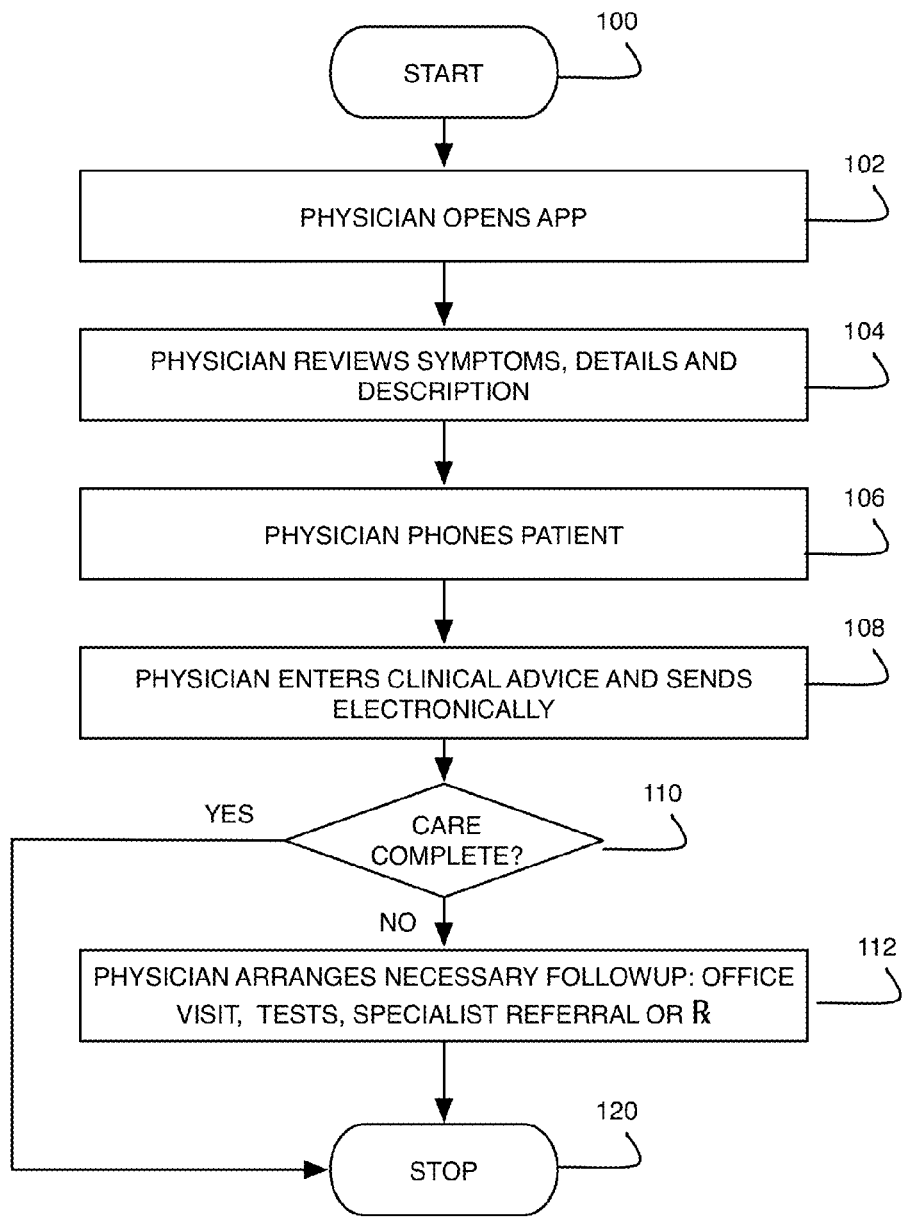
FIG. 4 shows a flowchart showing an example embodiment of a method for a physician accessing and providing care in the direct physician patient care delivery system according to the present disclosure.

FIG. 4 displays a flowchart of actions a physician performs in a system that provides delivery of medical care through instant patient access to a physician through a smartphone application (app) connecting over a network. The system eliminates a need for an administrative intermediary, closing a gap created by the intermediary in a healthcare relationship, thus establishing a direct doctor-patient relationship.

In block 100, the physician, having previously registered in the system and downloaded the app to the physician smartphone, starts the process when the app notifies the physician that a patient has entered the system and is pending.

Figure 9:
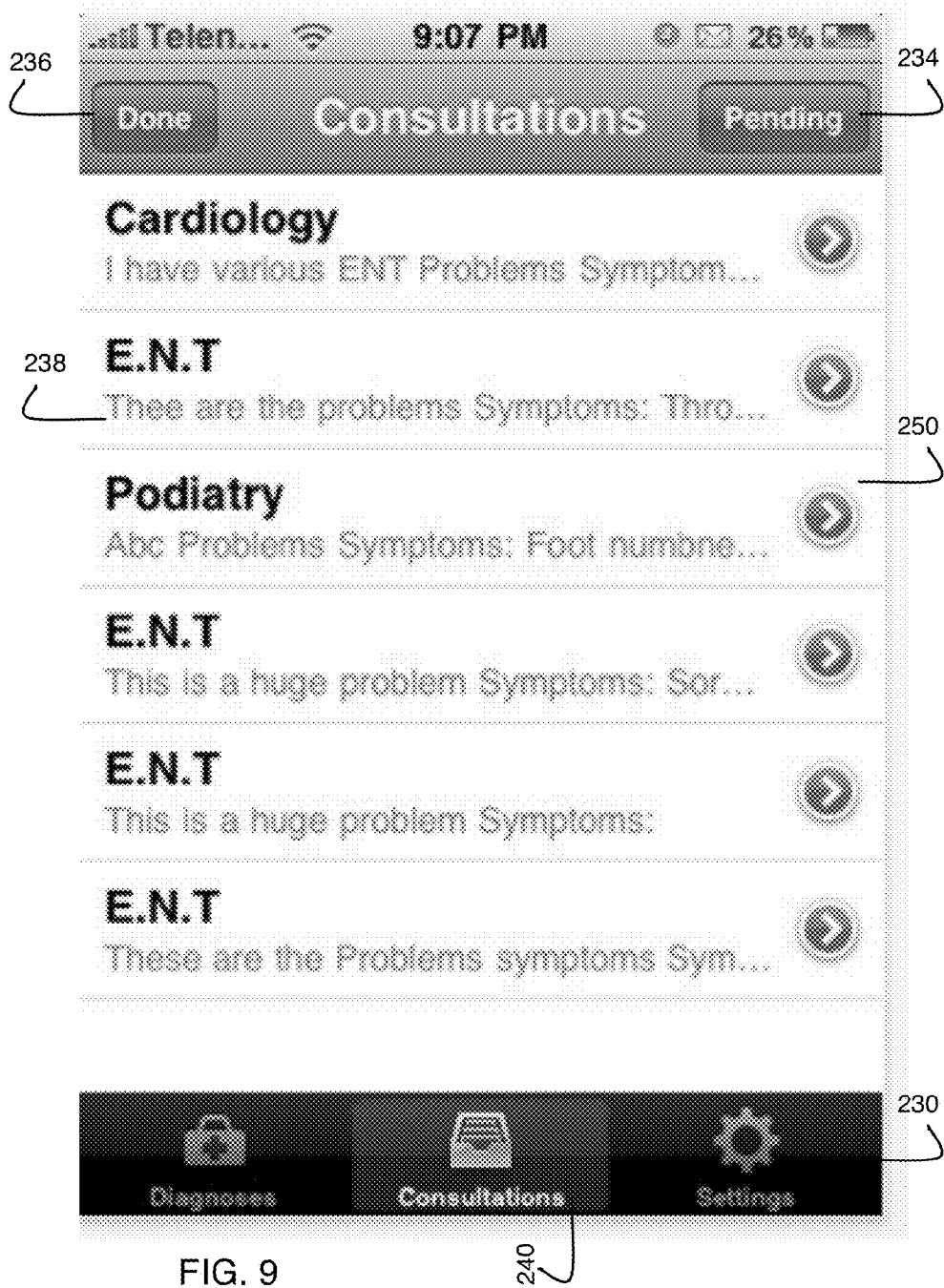
FIG. 9 shows an example display provided to a physician for reviewing a patient waiting list according to the present disclosure.

In block 102, the physician can open the app 102 and see a list of waiting patients. The list can include a brief summary summarizing the patient's submission. An example screen displaying a list of pending patients is shown in FIG. 9. The physician selects, such as by clicking, a patient from the pending patient to provide a consultation. The physician can also eject patients from the waiting list and can state a reason for doing so. The rejection and the reason can be communicated to the patient.

In block 104, the physician selects a patient, if more than one is waiting in the system, and reviews what the patient has entered, such as a plurality of symptoms, details, description, medical history, insurance details, and pharmacy details.

In block 106, the physician telephones the patient using the smartphone by selecting the telephone number in the patient record, causing the smartphone to dial the number. The physician consults with the patient directly, having all the necessary information displayed on the smartphone for a consultation. In one embodiment, the physician opens a second app to retrieve medical history, laboratory test results, digitized films of x-rays and other scans for assisting in diagnosis and assessment. The physician advises the patient on how to treat the condition, what medicines to take and activities to avoid. In another embodiment, using the smartphone or any other computing device, the physician videoconferences with the patient. The videoconference can be immediate or scheduled, manually or automatically, for a later time.

Figure 10:
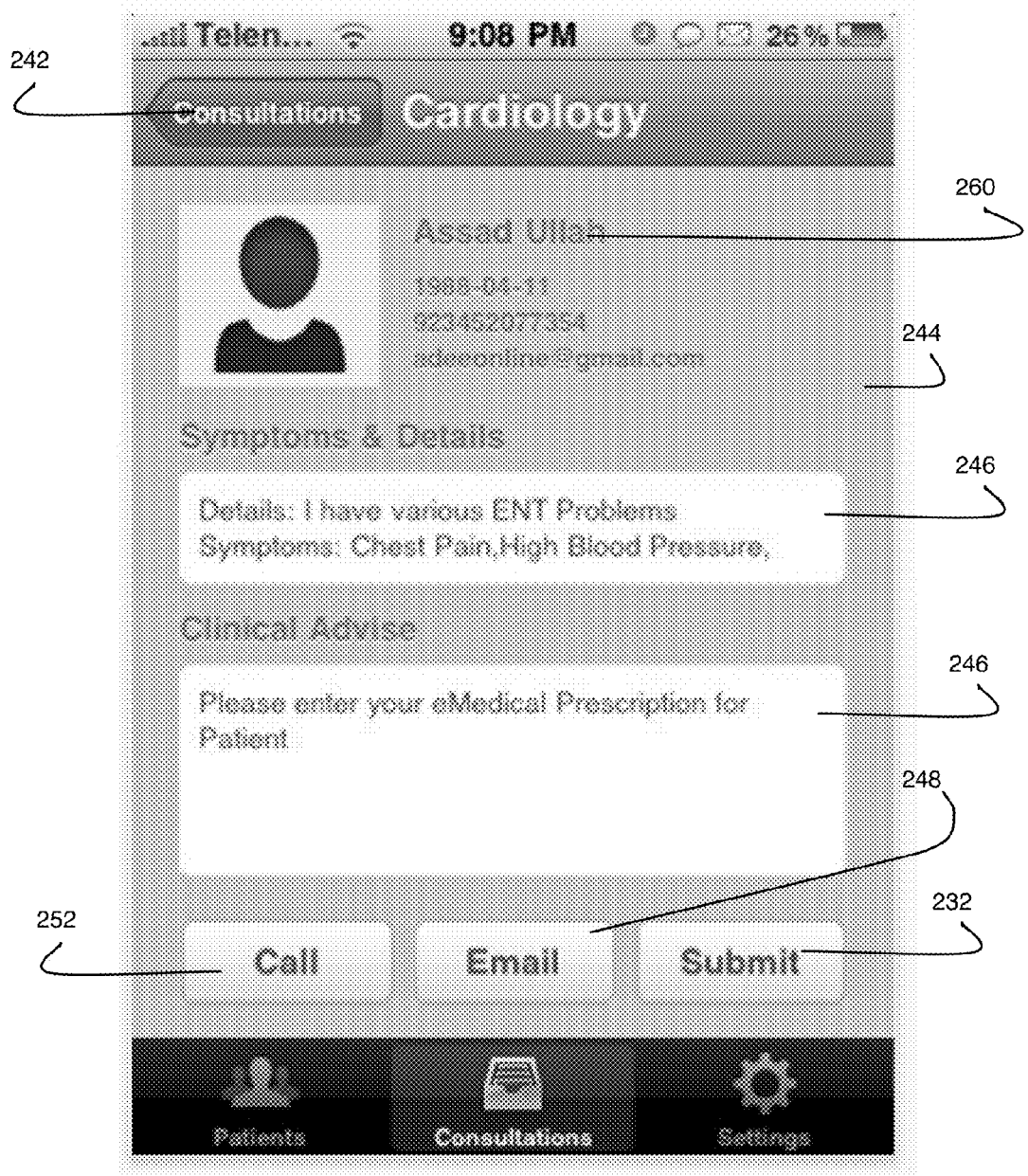
FIG. 10 shows an example display provided to the physician for entering clinical advice in writing according to the present disclosure.

In block 108, after orally delivering the clinical advice, the physician enters the clinical advice into the system, which sends the clinical advice electronically as an email or text message. The written advice allows the patient to review what the physician said, eliminating possible miscommunication if the patient does not hear or understand what the physician said during the consultation. An example consultation and advice display is shown in FIG. 10. In one embodiment the physician types the advice using the smartphone keyboard. In a further embodiment, the physician dictates the advice and the smartphone enters the dictated advice into the email or text message, translating the oral input into written text.

In block 110, the physician decides, with patient input, if the consultation and clinical advice is sufficient for treating the patient. If the care is complete at the time for the presenting condition, then in block 120, the physician stops the interaction with the patient. The physician returns to the opening screen of the app and chooses the next patient waiting.

If the physician decides that the consultation and advice is not sufficient treatment, then in block 112 the physician can immediately arrange for a follow-up. If the patient needs an office visit, the physician can open a calendar app on the physician smartphone and schedule an appointment with the patient. If the diagnosis and assessment requires the patient have a laboratory, radiological or imaging test performed, then the physician can electronically order the test either through another app, or through text and email apps. Similarly, if treatment requires a prescription drug, the physician can electronically prescribe the drug either through another app, or through text and email apps, local, state (or province) or federal law permitting. If the physician wishes to consult with another physician or refer the patient to a specialist, the physician can transfer the patient record to the app on the other physician's or specialist's smartphone if the other physician or specialist participating in a virtual clinic as described herein. After the physician completes the follow-up and stops, the physician returns to the opening screen of the app and chooses the next patient waiting.

Figure 3:
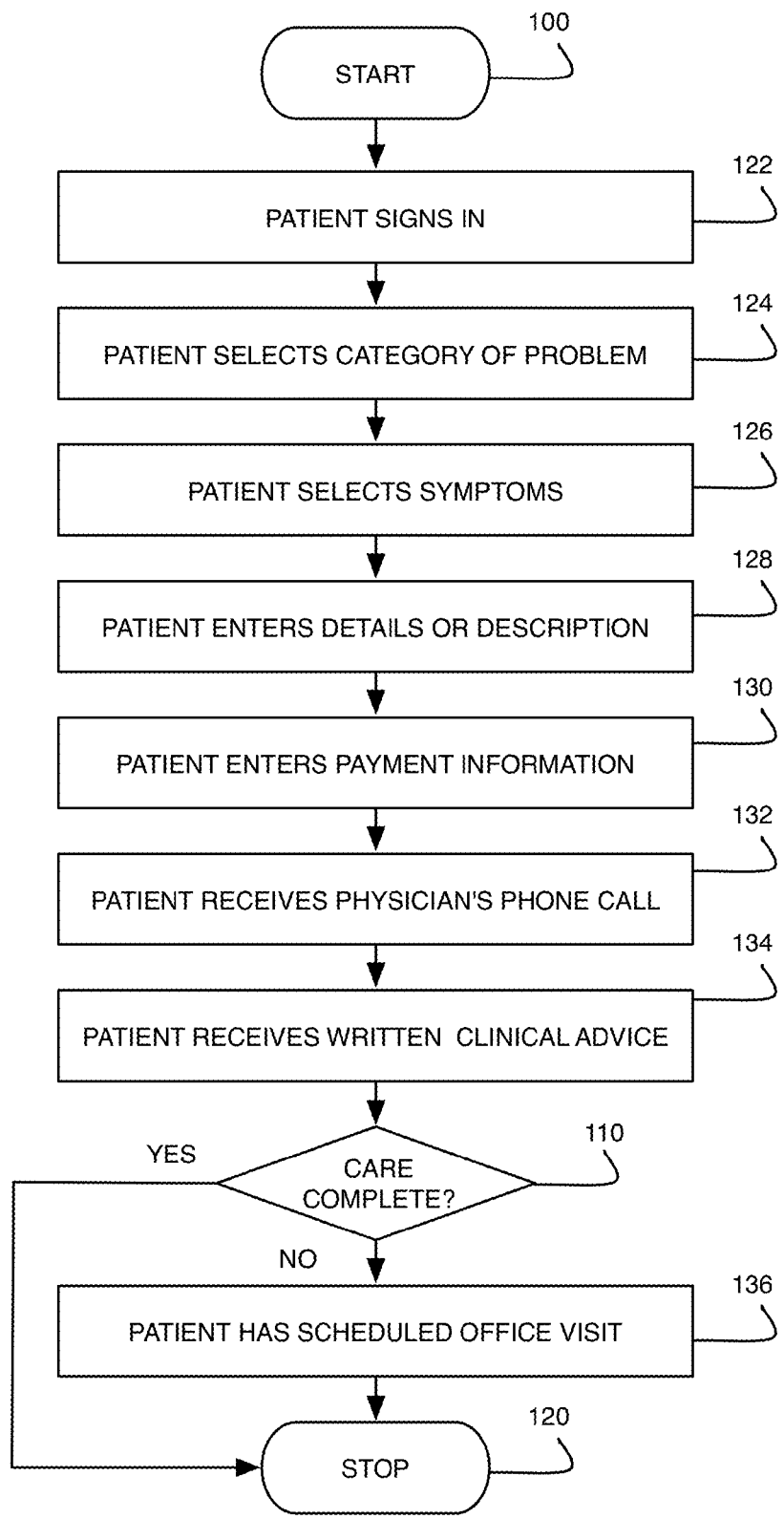
FIG. 3 shows a flowchart showing an example embodiment of a method for a patient accessing and receiving care in the direct physician patient care delivery system according to the present disclosure.

FIG. 3 shows a flowchart of actions a patient performs in the system. In a first non-limiting example, the patient uses the application on a patient smartphone, having installed the app and registered previously with the system.

In block 100, when the patient needs medical care, the patient starts the app. The app can be identical on both computing devices or be different on both computing devices. For example, the app can have different screens depending on the submitted login information.

Figure 7:
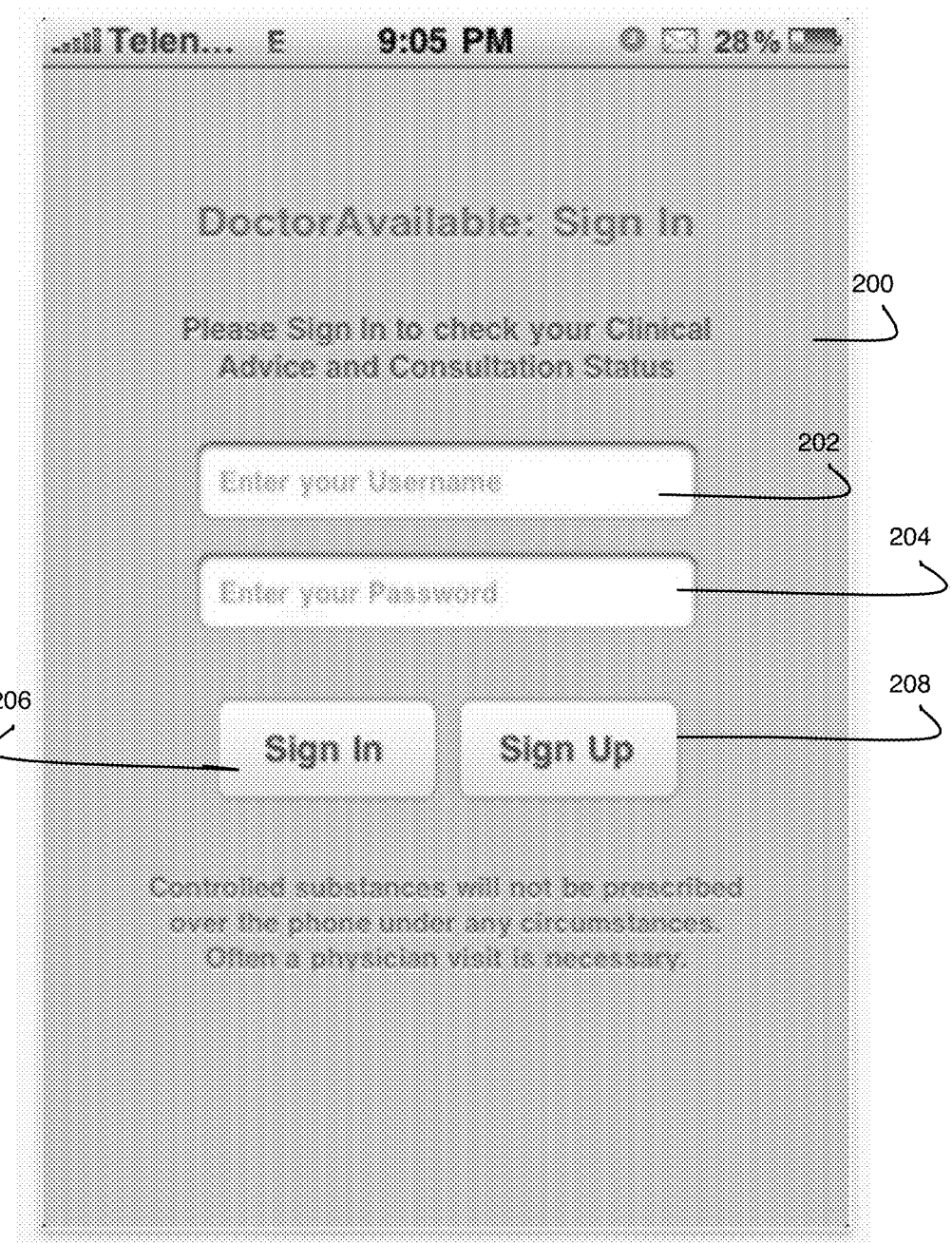
FIG. 7 shows an example display provided to a patient for signing in according to the present disclosure.

In block 122, the patient signs into the system 122 through the app. An example sign-in display is shown in FIG. 7. In an example embodiment, to open up an account in the system, the patient enters personal details, contact details, health insurance details and any other relevant details. In another example embodiment, the patient signs in into the system via an pre-existing social network profile.

In block 124, the app allows the patient to select the category of the problem by displaying a menu. The menu displays a plurality of categories for the patient to choose from, such as cardiology, E.N.T. (otolaryngology), urology, gastroenterology, neurology, gynecology, surgical or allergy.

In block 126, the patient selects symptoms from a second menu, the app presenting common symptoms associated with the category.

In block 128, the patient can further enter a plurality of details of the symptoms or describe how the symptoms present by typing or entering text.

Figure 8:
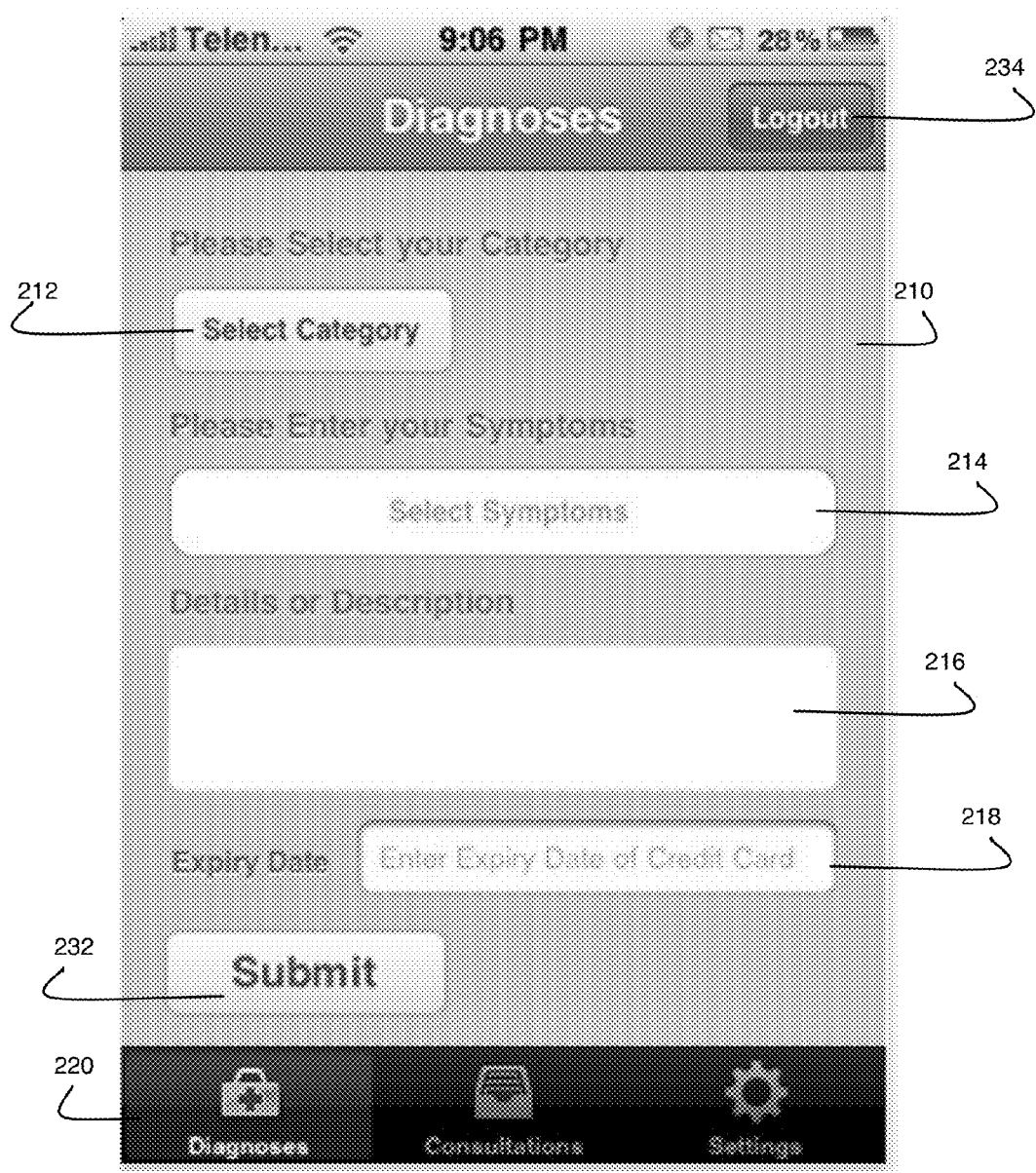
FIG. 8 shows an example display provided to a patient for entering symptoms according to the present disclosure.

In block 130, the patient enters credit card information for payment of a fee or a co-payment. An example screen display for selecting the category, selecting the symptoms, entering details or description and payment information is shown in FIG. 8.

In block 132, once the patient enters and submits all the information, the patient receives a telephone call from the physician. The patient consults with the physician and receives clinical advice orally from the physician. In another example embodiment, the patient can select which physician will review the submitted information. For example, the patient can search, with or without filters, for physicians via the system. Also, the patient can create bookmarks for found physicians or create a default physician.

In block 134, the patient receives an email (electronic mail) or text message with the written advice from the physician. The written advice allows the patient to review the treatment after the consultation, especially if the patient did not hear or understand what the physician said. Many patients are nervous when speaking to a doctor, even when not present in a treatment room, because of the "white coat" syndrome. The written advice allows the patient to review the advice or ask another to read and review if the patient needs assistance in performing any of the treatment steps given in the clinical advice. Since the patient can refer back to the clinical advice during the treatment period, patient compliance with the treatment protocol increases. The patient can email or send a text message for further clarification.

In block 110, if the physician, with the input of the patient, decides that the care is complete, then in block 120 the consultation ends and the patient follows the advice of the physician including any follow-up such as obtaining prescription medicines, scheduling laboratory, radiological or imaging tests, these activities not within the system of the present disclosure. If the decision is that an office visit is necessary, the physician uses a calendar app, whether linked or unlinked to the system, on the physician smartphone to schedule the office visit on the calendar app of the patient smartphone, as described with reference to block 112 of FIG. 3. In another example embodiment, the physician can send/receive text messages with the patient after the email regarding the clinical advice.

In block 136, the patient then makes an office visit to the physician as scheduled and the process ends at block 120.

In an example embodiment, the patient uses a web browser to connect to a website of the app if the patient does not have access to a smartphone running the app of the present disclosure. In a further example, the patient downloads the app onto a computing device such as, for example, but not limited to, a laptop computer, a mobile phone, a tablet computer, a personal digital assistant (PDA) or a desktop computer to enter the information as described herein through the smartphone app. The configuration and interconnection of such personal computing device can be varied, and substituted with other technologies both presently available and subsequently available, while adhering to the principles of the present disclosure.

Figure 6A:
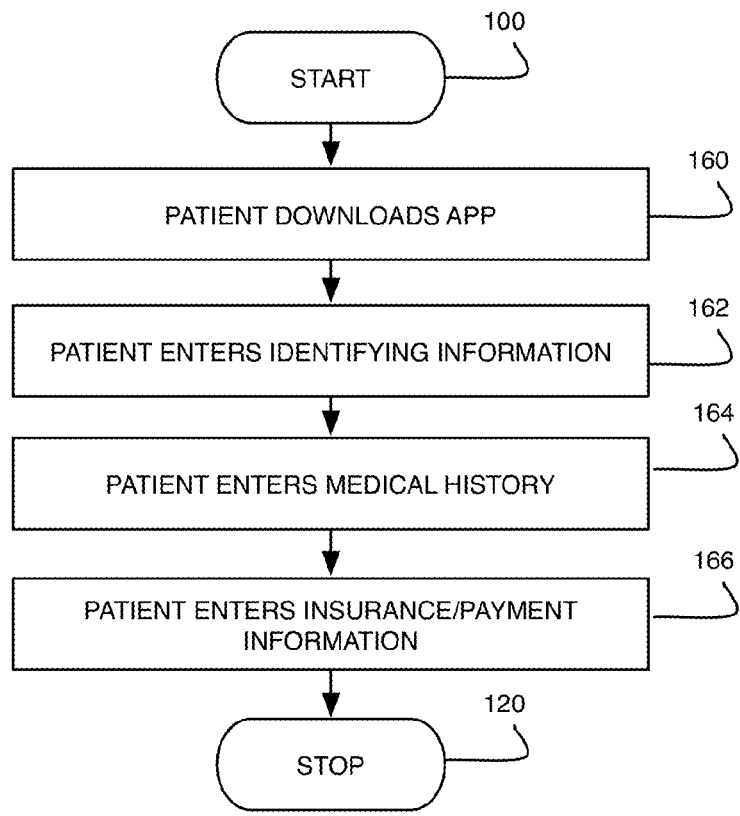
FIG. 6A shows a flowchart showing an example embodiment of a patient registering in the direct physician patient care delivery system according to the present disclosure.

As shown in FIG. 6A, in block 100, the patient process requires that the patient register to start the process before the first consultation.

In block 160, the patient downloads the app onto the patient smartphone and chooses a sign up button initially.

In block 162, the patient enters identifying information, such as, for example, name, birthdate, gender, marital status, contact info, screen-names.

In block 164, the patient enters medical history of the patient and a plurality of medical histories of close relatives.

In block 166, the patient enters insurance and payment information, such as a credit card for co-payments.

In block 120, the patient stops the process and the patient is ready for the first consultation with a physician when needed.

Figure 6B:
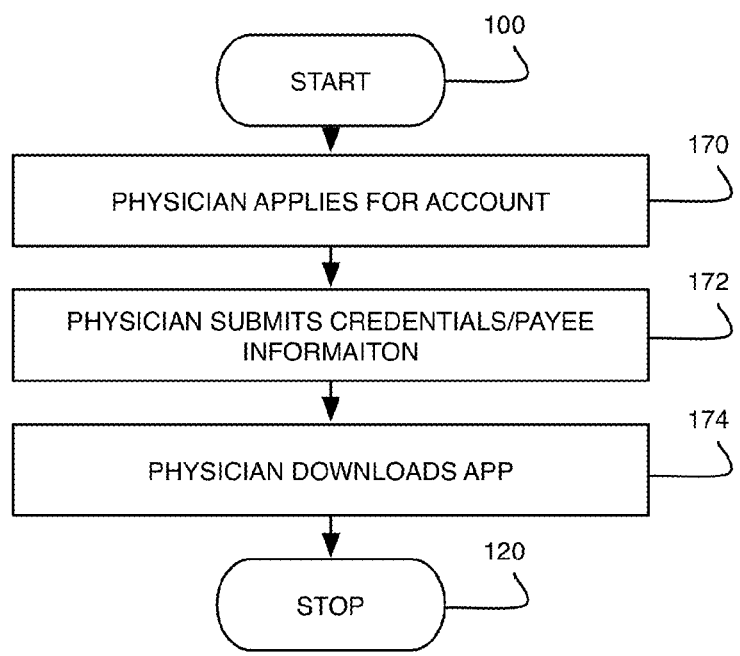
FIG. 6B shows a flowchart showing an example embodiment of a physician registering in the direct physician patient care delivery system according to the present disclosure.

As shown in FIG. 6B, in block 100, the physician who desires to use the system for providing healthcare to patients should register to start the process before the first consultation.

In block 170, the physician applies for an account. The application can include personal details, contact details, workplace details, banking details, health insurance details.

In block 172, the physician submits a plurality of credentials, such as licenses and certifications, as well as payee information, such as deposit accounts.

In block 174, once the system approves the physician, the physician can then download the app to the physician smartphone. Alternatively, the physician can download the app without approval, however, the physician is unable to provide advice until verified by the system. Verification can be performed via, for example, confirmation from a medical licensing authority, whether done manually or automatically.

Physicians can form a virtual clinic or virtual health maintenance organization (HMO) by linking together and sharing patient files, so that when the patient enters the system, the notification goes to the physician who treats patients in the category selected by the patient. If the patient selects the wrong category, the physician can re-categorize the complaint almost instantly, sending the complaint to a colleague that treats in the correct category in mere seconds. The virtual clinic is not confined to a particular geographic area, but can cross political borders. The virtual clinic can allow easy referrals to specialists by selecting the category of speciality after an initial consultation.

Figure 5:
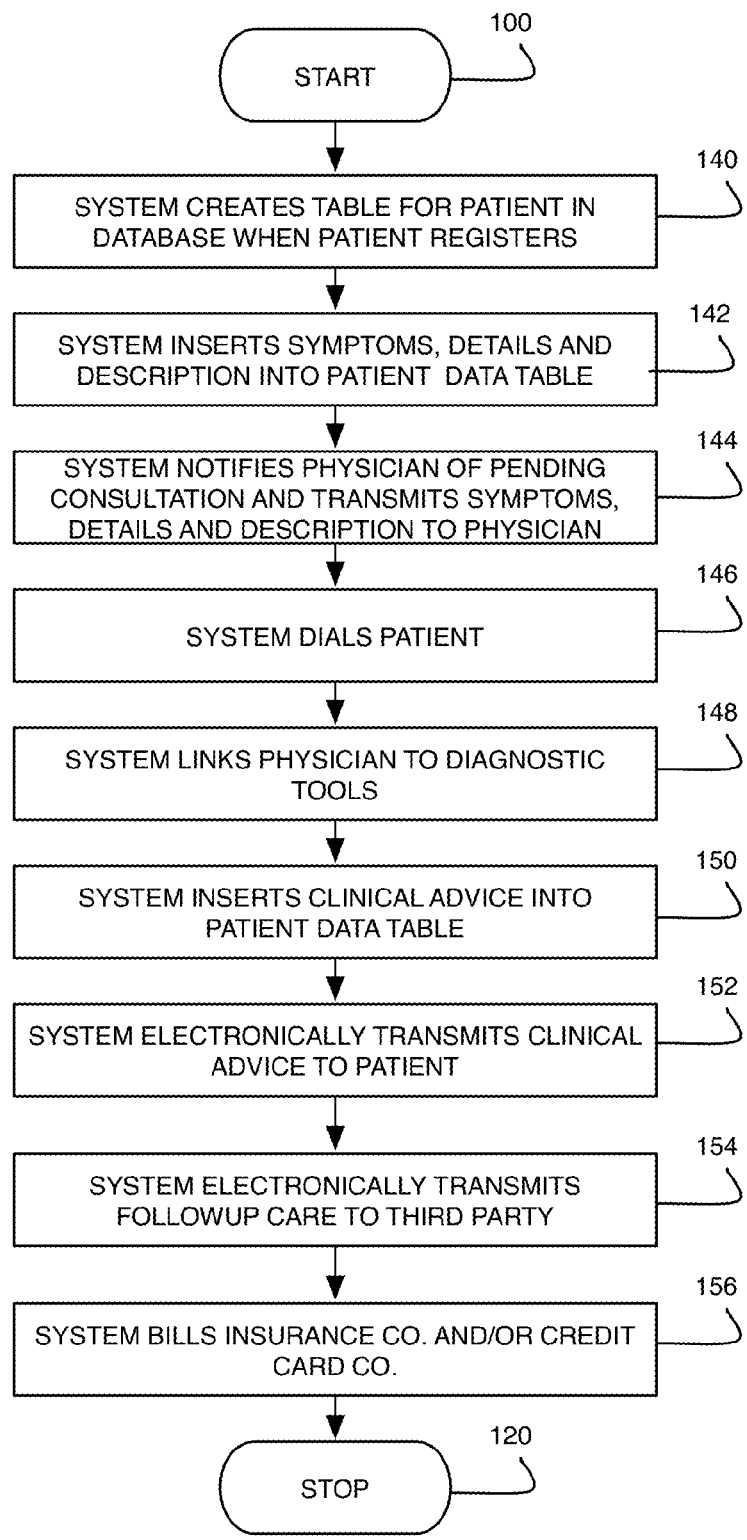
FIG. 5 shows a flowchart for an example embodiment of a system method in the direct physician patient care delivery system according to the present disclosure.

As illustrated in FIG. 5, in block 100, when a patient registers initially, then in block 140, the system creates a data table in a database for the patient with the information the patient entered.

In block 142, when the patient signs in with an issue or complaint and enters symptoms, details and descriptions of the issue or complaint, then the system inserts the symptoms, details and descriptions into the data table of the patient.

In block 144, the system notifies the physician of a pending consultation and transmits the symptoms, details and descriptions to the smartphone of the physician.

In block 146, when the physician selects the pending patient, then the system dials the patient and connects the patient and physician on a telephone call.

In block 148, the system selectively links the physician smartphone to diagnostic tools, such as laboratory or radiological test results or imaging scans.

In block 150, when the physician enters the clinical advice into the smartphone, then the system enters the advice into the data table of the patient.

In block 152, the system electronically transmits the clinical advice to the patient via email or text message.

In block 154, if required, then the system selectively transmits prescriptions and orders for follow-up care to third party providers, such as, for example, but not limited to, pharmacies, therapists, testing laboratories, radiological testing facilities, imaging facilities and specialists.

In block 156, the system bills a third party provider, such as insurance company, Medicare or Medicaid and bills the credit card company for the balance, if any, on the credit card of the patient. The transaction is complete and the system stops in block 120. It is understood by those of ordinary skill that the system is capable of processing a significantly large number of these transactions simultaneously so that the responses between patient and physician are sufficiently fast to appear to the patient as instantaneous.

FIG. 1 shows an example embodiment of a system 20. System 20 has a plurality of servers 30 connecting to Internet and to a smartphone cellular multimedia messaging system (MMS) 40 capable of transmitting multimedia messages and telephone calls. The physician and the patient have smartphones 60 capable of receiving multimedia messages and running the app and connecting to MMS 40.

It is understood that smartphones 60 connect both to a MMS cellular network 40 and the Internet through a wireless connection, but the MMS connection is illustrated here for simplicity and it demonstrated further herein. If the patient registers and enters information into the app through other personal computing devices, such as, a PDA 62, a laptop computer 64, or a table computer 66 as non-limiting examples of devices, the information flows through Internet 50 to servers 30 of system 20. The patient receives email containing the clinical advice through smartphone 60, PDA 62, laptop computer 64, or table computer 66. Alternatively, the patient receives the text message containing the clinical advice on smartphone 60 through MMS network 40. The configuration and interconnection of such devices can be varied, and substituted with other technologies both presently available and subsequently available, while adhering to the principles of the present disclosure.

Figure 2:
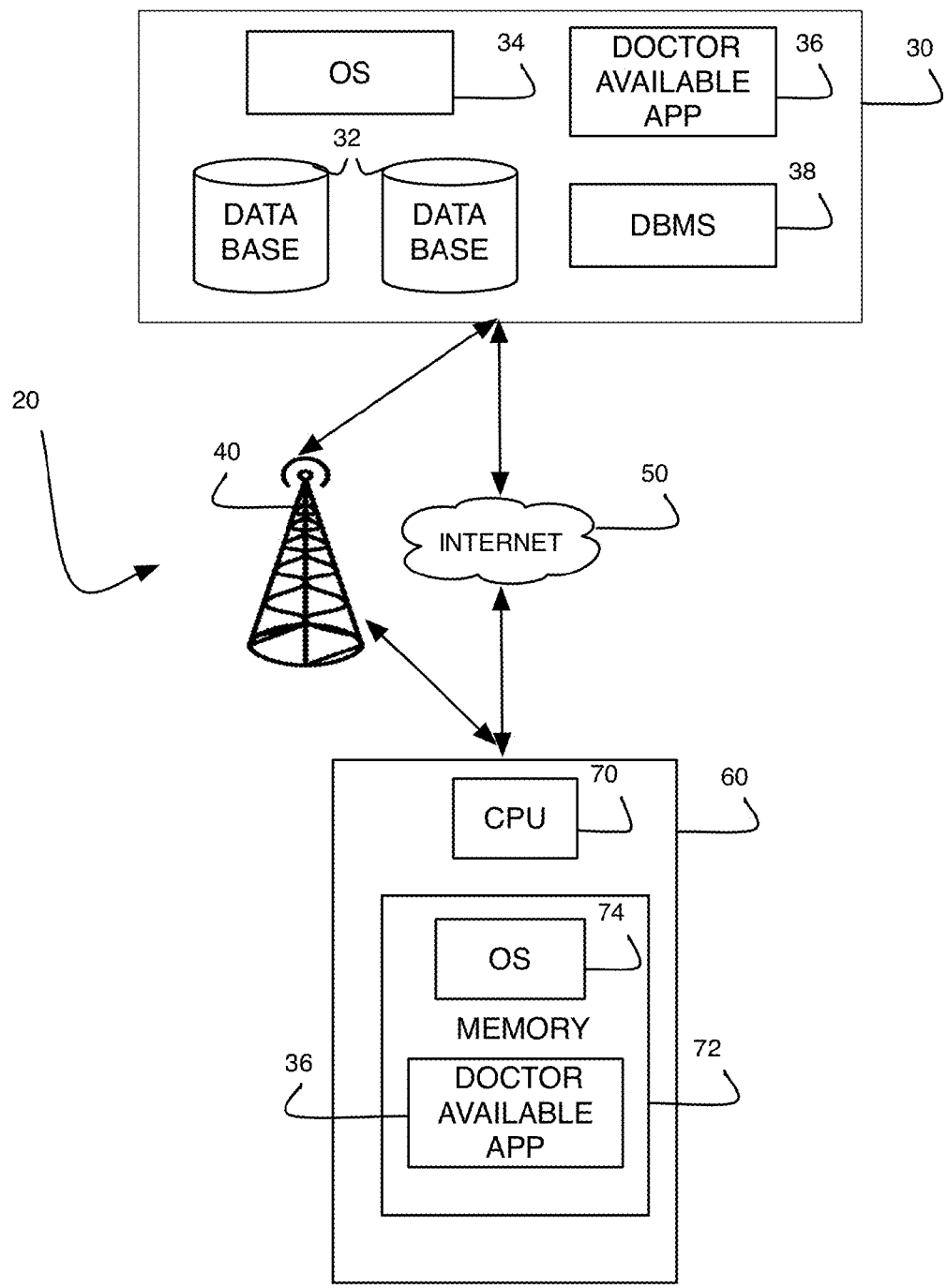
FIG. 2 shows a block diagram of an example embodiment of a direct physician patient care delivery system according to the present disclosure.

FIG. 2 is a block diagram of system 20, showing server 30 connecting to smartphone 60 of the patient and the physician through MMS network 40 or Internet 50.

Servers 30 each have software for operating system 20 that includes, but is not limited to, an operating system 34 with communications software for connecting to Internet 50 or to MMS network 40, drivers and other software utilities necessary for the servers to operate, which is well known to those of ordinary skill and the details of which are beyond the scope of this discussion.

Servers 30 store a plurality of databases 32 that include, but is not limited to, patient identification information, patient medical history and patient payment information. Servers 30 each have a database management system 38 for managing databases 32. Servers 30 have an application 36 of system 20.

Smartphone 60 has a central processing unit (CPU) 70 operably coupled to a memory 72 storing an operating system (OS) 74 with communications software for connecting to MMS network 40 and Internet 50, and other software utilities necessary for smartphone 60 to operate, and application 36 of system 20.

When the patient uses the personal computing device to enter symptoms, details and description and to receive email form the physician, the personal computing device, the device has CPU 70, memory 72, OS 74 with communications software for connecting to the Internet and application 36 of system 20. It is understood that the smartphone, personal computing device and server are not limited to these software and that other software programs on the smartphone, device and server, that are not necessary for the system, are beyond this discussion.

FIG. 7 displays an initial screen 200 presented to the patient when registering initially or signing-in for the consultation. When a patient initially registers, the patient selects a sign up button 208. The patient selects a sign in button 206 when subsequently using the app after the initial registration. The patient enters a username assigned at initial registration in a text entry box for username 202 and a password into a password text entry box 204. Those of ordinary skill in the art will understand that the illustrative displays discussed herein are to be interpreted in an example manner and that displays different from those shown and described herein can be used within the scope of the present disclosure. For example, features of the displays can be combined, separated, interchanged, and/or rearranged to generate other displays.

As shown in FIG. 8, once the required information is entered into the screen, a screen 210 as illustrated in an example manner is displayed to the patient. The patient selects a category of medicine from a menu 212 and selects symptoms from a menu of symptoms 214 associated with the category. The patient then can type or enter text into a details or description text entry box 216. The patient further enters credit card information into a text entry box 218 and selects a submit button 232.

Screen 210 has a bottom displaying a status bar, which indicates what portion of the process the patient is in. The status bar shows in a non-limiting example that the patient is in a diagnoses process as indicated by a diagnoses icon 220. After the patient submits the information, the patient can log out by selecting a logout button 234.

As shown in FIG. 9, the physician receives notice that there is a pending patient waiting. This notice can be of any type, such as a popup window or a side notification or any other type. The physician is in a consultation process, as indicated by a consultations icon 240 on the status bar on a consultations screen 250. Screen 250 shows a list of consultations 238. The physician selects a pending button 234 to see the pending consultations. Button 234 links to a screen showing the pending patient and the associated information. Upon selection of a button 230, the user or the patient, as determined by the login, can adjust setting of the app, as running on smartphone 60.

As shown in FIG. 10, a pending consultation screen 244 displays a user name 260 and the symptoms and details in one of boxes 246. The physician selectively calls the patient by selecting a call button 252. If the physician or the patient prefer, then the physician can choose to initially email the patient by selecting an email button 248. If the physician selects to call the patient, then, during or after the call, the physician enters the clinical advice into the other of boxes 246 for clinical advice and selects the email button 248, which sends the clinical advice by email or text message.

When the transaction is complete, as determined by at least one of the physician and the patient, then the physician selects a submit button 232 and the system completes the billing process. The physician returns to the list of consultations by selecting the button for consultations 242. The entire transaction between the patient and physician occurs in a timely manner through the direct communication possible in the system, appearing almost instantaneously to the patient.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate or transport a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments of the present disclosure. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The flow diagrams depicted herein are just one example. There may be many variations to this diagram or the steps (or operations) described therein without departing from the spirit of the disclosure. For instance, the steps may be performed in a differing order or steps may be added, deleted or modified. All of these variations are considered a part of the claimed disclosure.

While the preferred embodiment to the disclosure had been described, it will be understood that those skilled in the art, both now and in the future, may make various improvements and enhancements which fall within the scope of the claims which follow. These claims should be construed to maintain the proper protection for the disclosure first described In conclusion, herein is presented a system and method of providing delivery of medical care through instant patient access to a physician through an application on a smartphone connecting over a network. The present disclosure is illustrated by example in the drawing figures, and throughout the written description. It should be understood that numerous variations are possible. Such variations are contemplated as being a part of the present disclosure.

What is claimed is:

1. A method of delivering medical care, the method comprising:

maintaining, in a computer system, patient profiles associated with patients and physician profiles associated with physicians, each of the patient profiles including medical history, voice communication information and text communication information, each of the physician profiles including payee information;

receiving, from a first personal mobile computing device, medical symptoms and payer information associated with one of the patient profiles, the system storing the symptoms in the history of the one of the patient profiles, the first device operated by one of the patients, the first device running a software application in a patient mode, the patient mode having a symptom graphical user interface element operative to receive input for the symptoms, the patient mode having a payer graphical user interface element operative to receive input for the payer information;

causing the symptoms to be displayed on a second personal mobile computing device, the second device displaying a text field associated with one of the physician profiles, the system authorizing the physician associated with the one of the physician profiles to view the history of the one of the patient profiles, the second device operated by one of the physicians, the second device running the software application in a physician mode operative to display the symptoms and the text field;

causing a voice datalink to be established, from the second device via the physician mode, according to the voice information of the one of the patient profiles in order to provide oral consultation regarding the symptoms, the physician mode operative to display a voice datalink graphical user interface element configured to initiate the voice datalink in response to physician activation; and causing a clinical advice, as entered into the text field via the physician mode, to be sent according to the text communication information of the one of the patient profiles, the system storing the advice in the history of the one of the patient profiles, the advice memorializing the consultation, the system billing according to the payer information and the payee information of the one of the physicians, the physician mode operative to display a text field graphical user interface element configured to initiate sending contents of the text field in response to physician activation.

2. The method of claim 1, further comprising:

causing a patient waiting list associated with the one of the physician profiles to be displayed on the second device, the list listing indicia associated with the one of the patient profiles and another of the patient profiles, the system updating the list;

receiving acknowledgement of activation of one of the indicia corresponding to the one of the patient profiles and performing the causing the symptoms to be displayed on the second device; and causing an appointment to visit a physician associated with the one of the physician profiles to be scheduled on the second device, wherein the symptoms including at least one of a symptom detailed description and a symptom image.

3. The method of claim 2, further comprising:

receiving physician credentials for the one of the physician profiles;

verifying the credentials; and causing prescription data to be sent from the second device to a third party provider, the prescription data relating to treatment of the symptoms, the system storing the prescription data in the history of the one of the patient profiles, wherein the voice datalink is at least one of a phone call, a voice chat and a video teleconference.

4. The method of claim 3, further comprising:

causing a medical diagnostic test order for a patient associated with the one of the patient profiles to be placed on the second device;

receiving a result of the test, the system storing the result in the history of the one of the patient profiles, wherein the text communication information allowing at least one of printing out and mailing the advice, emailing the advice and texting the advice, the voices datalink between the second device and the first device.

5. The method of claim 4, further comprising:

authorizing the physician associated with another physician profile to view the history of the one of the patient profiles, the physician profiles including the another physician profile, wherein the patient profiles including medical insurance information, the payer information functioning as co-payment according to the insurance information of the one of the patient profiles.

6. The method of claim 5, further comprising:

causing a referral to be sent to a specialist physician profile associated with a specialist physician, the physician profiles including the specialist physician profile, the system authorizing the physician associated with the specialist physician profile to view the history of the one of the patient profiles, the system storing the referral in the history of the one of the patient profiles, wherein the symptoms including at least one of a medical category related to the symptoms and a common symptom associated with the category.

7. The method of claim 6, further comprising:

receiving data indicating a geographic location of the first device;

causing a map to be displayed on the first device, the map showing which of the physicians are near the location, the physician profiles including physician pictures and recommendations as recommended via some of the patient profiles, selecting the one of the physicians as a default physician;

wherein the system causing the history of the one of the patients to be displayed on the second device in chronological order.

8. The method of claim 7, further comprising:

authorizing the physician associated with the one of the physician profiles to view the history of other patient profiles associated with other patients biologically related to the patient, wherein the physician profiles including physician specialties.

9. The method of claim 8, further comprising:

removing the another of the patient profiles from the list in response to a removal action on the second device;

causing a stage indicator to be displayed on at least one of the first device and the second device, the indicator visually indicating a stage in the delivery of medical care, wherein the patient profiles including graphical representations of at least portion of the histories.

10. A system of delivering medical care, the system comprising:

a computer system storing patient profiles corresponding to patients and physician profiles corresponding to physicians, each of the patient profiles including medical history, voice communication information and text communication information, each of the physician profiles including payee information;

a first personal mobile computing device running a first instance of a software application having a patient mode and a physician mode, the patient mode initiated via a patient login corresponding to one of the patient profiles of one of the patients, the physician mode initiated via a physician login corresponding to one of the physician profiles of one of the physicians, the first instance running in the patient mode, the first instance sending medical symptoms and payer information to the computer system, the computer system storing the symptoms in the history of the one of the patient profiles, the patient mode having a symptom graphical user interface element operative to receive input for the symptoms, the patient mode having a payer graphical user interface element operative to receive input for the payer information;

a second personal mobile computing device running a second instance of the application in the physician mode, the second instance displaying the symptoms and a text field, the computer system authorizing the physician associate with the one of the physician profiles to view the history of the one of the patient profiles, the second instance establishing a voice datalink according to the voice information of the one of the patient profiles in order to provide oral consultation regarding the symptoms, the second instance sending a clinical advice, as input into the text field, according to the text communication information of the one of the patient profiles, the advice memorializing the consultation, the computer system storing the advice in the history of the one of the patient profiles, the computer system billing according to the payer information and the payee information of the one of the physicians, the physician mode operative to display a voice datalink graphical user interface element configured to initiate the voice datalink in response to physician activation, the physician mode operative to display a text field graphical user interface element configured to initiate sending contents of the text field in response to physician activation.

11. The system of claim 10, wherein the second instance displaying a patient waiting list associated with the one of the physician profiles, the list listing indicia corresponding to the one of the patient profiles and another of the patient profiles, the computer system updating the list, the computer system receiving acknowledgement of activation of one of the indicia corresponding to the one of the patient profiles and, in response, the second instance displaying the symptoms, the second instance scheduling an appointment to visit a physician associated with the one of the physician profiles, the symptoms including at least one of a symptom detailed description and a symptom image.

12. The system of claim 11, wherein the second instance sending prescription data to a third party provider, the prescription data relating to treatment of the symptoms, the computer system storing the prescription data in the history of the one of the patient profiles, the voice datalink is at least one of a phone call, a voice chat and a video teleconference.

13. The system of claim 12, wherein the second instance placing a medical diagnostic test order for a patient associated with the one of the patient profiles, the computer system receiving a result of the test and storing the result in the history of the one of the patient profiles, the text communication information allowing for at least one of printing out and mailing the advice, emailing the advice and texting the advice, the voice datalink between the second device and the first device.

14. The system of claim 13, wherein the computer system authorizing the physician associated with another physician profile to view the history of the one of the patient profiles, the physician profiles including the another physician profile, each of the patient profiles including medical insurance information, the payer information functioning as co-payment according to the insurance information of the one of the patient profiles.

15. The system of claim 14, wherein the second instance sending a referral to a specialist physician profile associated with a specialist physician, the physician profiles including the specialist physician profile, the computer system authorizing the physician associated with the specialist physician profile to view the history of the one of the patient profiles, the computer system storing the referral in the history of the one of the patient profiles, the symptoms including at least one of a medical category related to the symptoms and a common symptom associated with the category.

16. The system of claim 15, wherein the computer system receiving data indicating a geographic location of the first device, the first instance displaying a map showing which of the physicians are near the location, the physician profiles including physician pictures and recommendations as recommended via some of the patient profiles, the first instance selecting the one of the physicians as a default physician, the computer system causing the history of the one of the patients to be displayed via the second instance in chronological order.

17. The system of claim 16, wherein the computer system authorizing the physician associated with for the one of the physician profiles to view the history of other patient profiles associated with other patients biologically related to the patient, the physician profiles including physician specialties.

18. The system of claim 17, wherein at least one of the first instance and the second instance displaying a stage indicator visually indicating a stage in the delivery of medical care, the patient profiles including graphical representations of at least portion of the histories.

19. A method of delivering medical care, the method comprising:

inputting a medical symptom and payer information associated with a patient profile into a patient mode of a software application running on a first personal mobile computing device, the patient profile including medical history, voice communication information and text communication information, the first device operated by a patient associated with the patient profile, the patient mode having a symptom graphical user interface element operative to receive input for the symptoms, the patient mode having a payer graphical user interface element operative to receive input for the payer information;

sending the symptoms and the payer information to a computer system for storing the symptoms in the history and the payee information in the patient profile;

retrieving, via a second personal mobile computing device, the symptom from the system and displaying the symptom and a text field in a physician mode of the software application running on the second device, the text field associated with a physician profile storing payee information, the second device operated by a physician associated with the physician profile;

authorizing, via the system, the physician associated with the physician profile to view the history;

establishing a voice datalink, from the second device, according to the voice information in order to provide oral consultation regarding the symptoms, the physician mode displaying a voice datalink graphical user interface element operative to initiate the voice datalink in response to physician activation;

sending a clinical advice, as entered into the text field, according to the text communication information, the advice memorializing the consultation, the physician mode displaying a text field graphical user interface element operative to initiate sending contents of the text field in response to physician activation;

storing, via the system, the advice in the history; and billing, via the system, according to the payer information and the payee information.

20. The method of claim 19, further comprising:

displaying a patient waiting list of the physician profile on the second device, the list listing indicia associated with the patient profile and another patient profile;

in response to activating one of the indicia corresponding to the patient profile, displaying the symptom on the second device;

scheduling, via the second device, an appointment to visit a physician associated with the physician profile;

sending prescription data from the second device to a third party provider, the prescription data relating to treatment of the symptoms, the system storing the prescription data in the history;

placing, via the second device, a medical diagnostic test order for the patient profile;

authorizing, via the system, the physician associated with another physician profile to view the history, the patient profile including medical insurance information, the payer information functioning as co-payment according to the insurance information of the one of the patient profiles; and displaying, on at least one of the first device and the second device, a stage indicator visually indicating a stage in the delivery of medical care.

* * * * *